United States Patent [19]
Theoharides

[11] Patent Number: 5,855,884
[45] Date of Patent: Jan. 5, 1999

[54] TREATMENT OF STRESS-INDUCED MIGRAINE HEADACHE WITH A CORTICOTROPIN RELEASING HORMONE BLOCKER

[75] Inventor: Theoharis C. Theoharides, Brookline, Mass.

[73] Assignee: KOS Pharmaceuticals, Inc., Miami, Fla.

[21] Appl. No.: 562,873

[22] Filed: Nov. 27, 1995

[51] Int. Cl.$^6$ ............................ A61K 39/395; A61K 38/00
[52] U.S. Cl. ........................................ 424/130.1; 424/139.1; 424/158.1; 514/12; 514/13; 514/14; 514/15; 514/16; 514/17; 514/18; 514/19; 530/388.24; 530/389.2
[58] Field of Search ................... 514/12–19; 424/139.1, 424/130.1, 158.1; 530/388.24, 389.2

[56] References Cited

U.S. PATENT DOCUMENTS 5,250,529   10/1993   Theoharides ............................ 514/255

OTHER PUBLICATIONS

W. Boucher et al., "Corticotropin Releasing Hormone (CRH) Induces Rat Mast Cell (MC) Secretion", Tufts University Experimental Biology 95 Abstract Form, May 1995.
E. Webster et al., "The Mast Cell as a Target of Peripheral Immune Corticotrophin–Releasing Hormone (CRH) and Mediator of its Proinflammatory Properties: Clinical Implications", The Endocrine Society Abstract Form, Jun. 1995.
T. Theoharides, "Tufts Researcher Uncovers Link Between Stress and Migraines", Tufts University, Nov. 28, 1995, pp. 1–4.
T. Theoharides et al., "Stress–Induced Inracranial Mast Cell Degranulation: A Corticotrophin–Releasing Hormone–Mediated Effect", Endocrinology, vol. 136, No. 12, Dec. 1, 1995, pp. 5745–5750.

*Primary Examiner*—Sheela Huff
*Attorney, Agent, or Firm*—Foley & Lardner

[57] ABSTRACT

Non-traumatic immobilization (restrain) stress causes rapid degranulation of rat dura mast cells, as shown both by light and electron microscopy. These morphologic findings were accompanied by elevation of rat mast cell protease cerebrospinal fluid. Mast cell activation due to stress was abolished in animals that had been treated neonatally with capsaicin, indicating that neuropeptides in sensory nerve endings are involved in this response. Complete inhibition was also achieved by pretreating the animals intraperitoneally with antiserum to corticotropin releasing hormone (CRH). Mast cells in the dura were localized close to nerve processes containing substance P, but no CRH-fibers were identified even though these were found close to mast cells elsewhere in the brain, i.e., in the median eminence. This is the first time that stress is shown to activate intracranial mast cells, apparently through the sequential actions of CRH and one or more sensory neuropeptides such as Substance P. These findings suggest that therapy of neuroinflammatory disorders such as stress-induced migraine headaches, can be achieved with blockers of the physiological actions of CRH or inhibitors of CRH production or secretion.

12 Claims, 5 Drawing Sheets

FIG. IA
FIG. IB
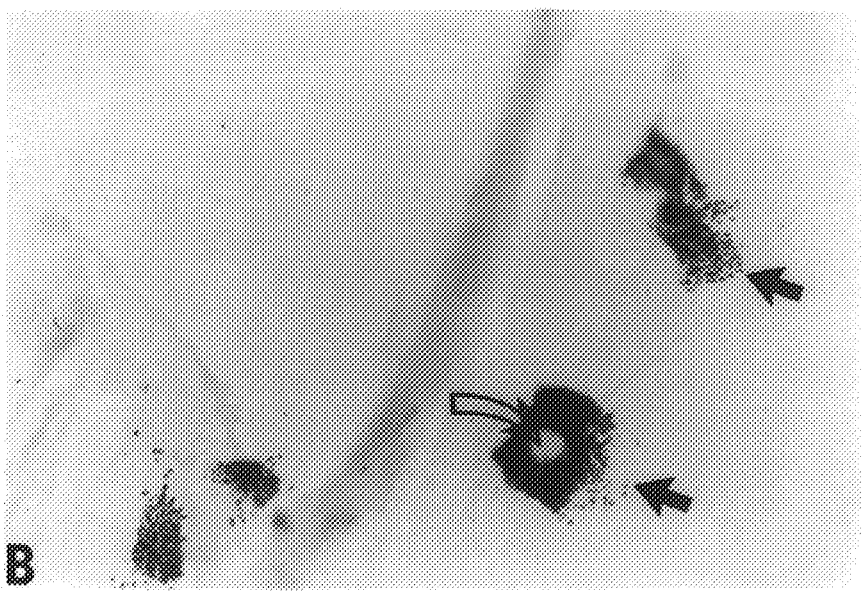

TREATMENT OF STRESS-INDUCED MIGRAINE HEADACHE WITH A CORTICOTROPIN RELEASING HORMONE BLOCKER

FIELD OF THE INVENTION

This invention relates to a method of treatment of migraine headaches. More particularly, it relates to the treatment of stress-induced migraine headaches with agents that inhibit the action or actions of the neuroendocrine polypeptide, corticotropin releasing hormone.

BACKGROUND OF THE INVENTION

Migraine headaches are known to produce the most intense headaches reported. The pathophysiology of migraine headaches involve vasoconstriction and vasodilation. A variety of stress stimuli, including intense light, noise, anxiety, exertion, extremes of temperature, hormones, exhaustion, infection and trauma result in constriction of extracranial blood vessels. The vasoconstriction is followed by reflexive or sequential vasodilation, which subsequently spreads to intracranial vessels. It is during this latter phase that the patient feels the intense, throbbing headache characteristic of migraines. Increased levels of norepinephrine, serotonin, histamine, and the neuropeptides bradykinin and substance P, in addition to products of tissue anoxia, are considered to be the main endogenous pain producing molecules, accompanied by direct sensory nerve stimulation because of the stretching that accompanies vasoconstriction and dilation.

Mast cells, normal components of connective tissues, are thought to play an important role in the development of migraine headaches (see, e.g., Theoharides, U.S. Pat. No. 5,250,529). Each mast cell contains as many as 500 secretory granules, each storing over 20 different kinds of biochemicals, including histamine, neuropeptide kinins, prostagandims $PGP_2$, $PGD_4$, leukotriene $C_4$, and serotonin which are vasoconstrictive, as well as vasodilatory, vasoactive intestinal polypeptide, tumor necrosis factor and nitric oxide. Degranulation of mast cells, which is defined herein as the release of any or all biochemicals from secretory granules to the local tissue area or circulation, for whatever reason in whatever sequence, occurs in response to interaction of various agents with specific mast cell surface receptors or other binding proteins. The best known of these receptors is the one for immunoglobulin E (IgE). There is also evidence that neurotransmitters such as acetylcholine and neuropeptides, released from neurons, and female sex hormones (estradiol) may also trigger mast cell degranulation through specific receptors, especially in response to stress. Other known triggers include viruses, bacterial toxins, drugs such as aspirin, morphine and curare, radiological contrast media, extremes of temperature, solar radiation, etc. A method of alleviating or preventing a migraine headache comprising the administration of a direct mast cell degranulation blocking agent during the prodromal phase of the migraine and in the absence of an analgesic is the subject of the aforementioned U.S. Pat. No. 5,250,529.

Stress is long known to activate the hypothalamic-pituitary-adrenal axis and can affect illness, especially autoimmune and neuroinflammatory syndromes. These effects may be mediated both through psychoneuroimmune and neuroendocrine-immune interactions which contribute to inflammation and inflammatory diseases. Stress precipitates or worsens certain neuroinflammatory conditions such as migraines (Theoharides, *Prospect. Biol. Med.,* 26:672 (1983)), and interstitial cystitis (Sant et al., Urol. Clin. North Amer., 21:41–53, (1994)), both of which have been associated with mast cell activation. Mast cells are necessary for the development of allergic and late phase reactions, but may be involved in inflammation as they release numerous cytokines (Galli, *N. Eng. J. Med.,* 328:257 (1993)). Mast cells have also been found in close apposition to neurons and, as noted above, are activated by neuropeptides, as well as by antidromic nerve stimulation in the dura. Moreover, mast cell secretion of histamine occurs after repetitive exposure to odors, after Pavlovian conditioning and in response to isolation stress (Bugajski et al., *Agents Actions,* 41:C75–76 (1994)). These findings have raised speculations that mast cells may be involved in neuroimmunoendocrine physiology (Stead et al., in Burger et al., eds. Cell to Cell Interaction, Karger, Basel, 1990, pp 170–187) and pathology (Theoharides, *Life Sci.,* 46:607 (1990)).

It is, therefore, an object of this invention to describe the biochemical and anatomical link between stress and the development of migraine headaches, and to provide pharmaceutical means for disrupting this link.

SUMMARY OF THE INVENTION

This object has been achieved, using an animal model of nontraumatic restrain stress previously known to activate the hypothalamic-pituitary axis, by the unexpected discoveries that: stress activates mast cells in the brain dura where they have been implicated in the pathophysiology of migraine headaches; corticotropin releasing hormone (CRH) indirectly mediates stress-induced intracranial mast cell degranulation and consequent migraine headaches; and agents that interfere with the physiological actions of CRH, such as anti-CRH and anti-CRH mast cell receptor antibodies and competitive inhibitors of the binding of CRH to active sites, unexpectedly inhibit stress-induced migraine headaches indirectly through the regulation of neuropeptides and neurotransmitters that trigger the degranulation of intracranial mast cells.

It is an aspect of this invention, therefore, to provide pharmaceutical compositions containing one or more CRH blockers for the treatment of stress-induced migraine headaches.

DESCRIPTIONS OF THE FIGURES

FIGS. 1A and 1B. FIG. 1A is a photomicrograph of control dura mast cells stained with toluidine blue. FIG. 1B is the same photomicrograph obtained from tissue from a stressed rat. Magnification 1000×.

FIGS. 2A–2C. FIG. 2A shows mast cells stained metachromatically violet by toluidine blue, adjacent to SP-immunoreactive nerve processes (stained brown) in the control dura. Magnification 1000×. FIG. 2B (200×) shows CRH-immunoreactive nerve processes (stained golden-brown) close to a mast cell stained with toluidine blue in the median eminence of the hypothalamus. FIG. 2C (200×) shows negative CRH immunohistochemistry in the dura.

FIG. 3 is an electronmicrograph showing portions of two mast cells from dura surrounding a neuronal (N) terminal process containing numerous synaptic vesicles (small solid arrows). The mast cell granules (g) contain heterogeneous electron dense materials, whereas some are surrounded by clear space suggestive of secretory activity (upper mast cell). Magnification 230,000×.

FIGS. 4A–4D. FIG. 4 shows electron photomicrographs of mast cells from dura. FIG. 4A shown control animals;

note, multiple, homogeneous, intact, electron-dense granules (magnification 13,800×). FIGS. 4B (16,800×), 4C (16,800×) and 4D (30,900×) are stressed animals; note many granules are altered and contain less electron-dense material, demonstrating degranulation.

DETAILED DESCRIPTION OF THE PREFERRED EMBODIMENTS

Figures 2A, 2B, 2C:
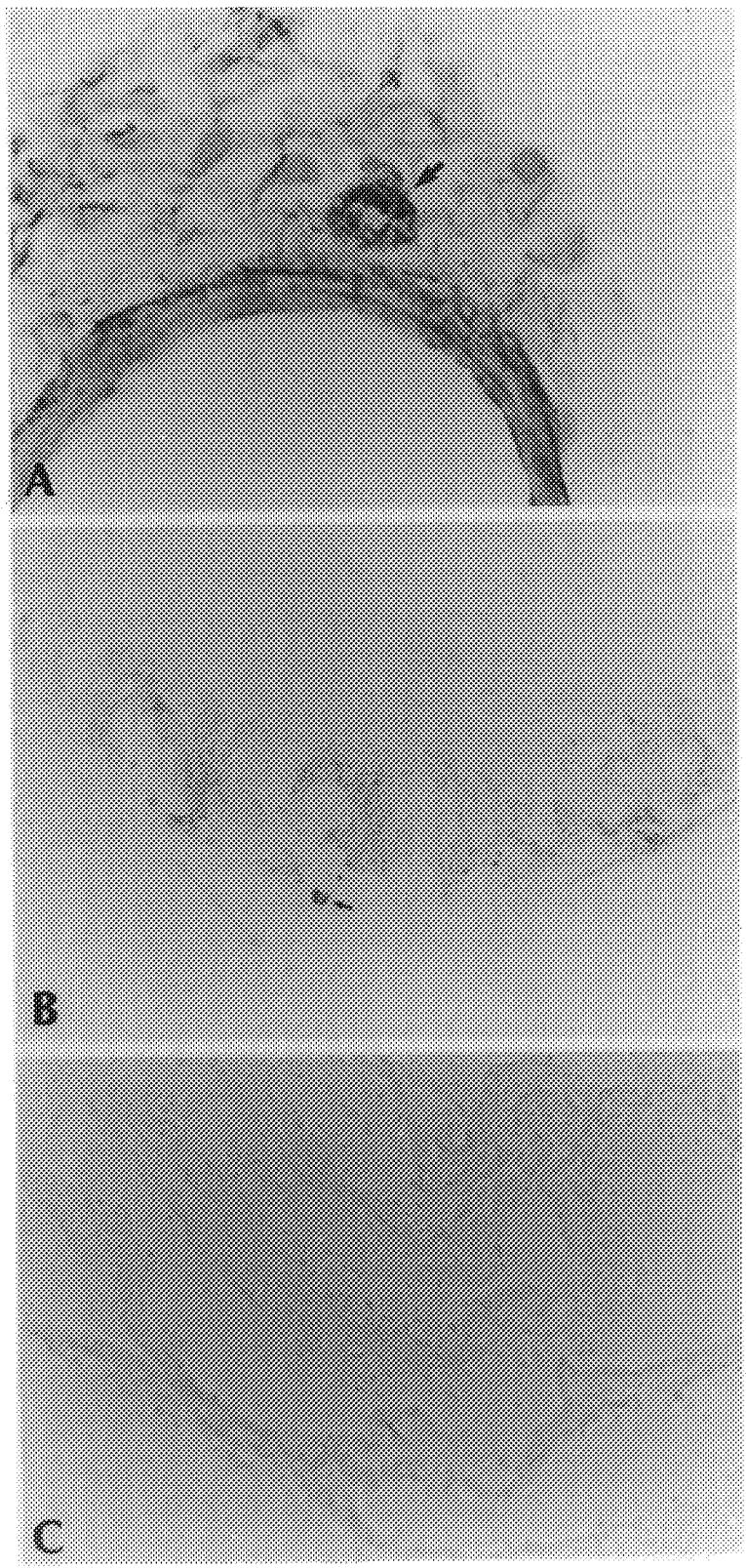

As noted above, stress is known to precipitate or worsen a number of disorders, such as migraines, in which mast cells are suspected of being involved, by indirectly releasing vasoactive, nociceptive and proinflammatory mediators. However, no functional association has previously been demonstrated between a migraine trigger and brain mast cell activation. Non-traumatic immobilization (restrain) stress is known to stimulate the hypothalamic-pituitary-adrenal axis, and cause redistribution of immune cells. Here, restrain stress caused degranulation in 70% of rat dura mast cells within 30 minutes (which is the timeframe during which a migraine typically develops), as shown both by light and electron microscopy. These morphologic findings were accompanied by cerebrospinal fluid elevation of rat mast cell protease I, but not II, indicating secretion from connective tissue type mast cells, such as those found in the dura, the meningeal membrane found closest to the skull.

Mast cell activation due to stress was abolished in animals that had been treated neonatally with capsaicin, indicating that such neuropeptides in sensory nerve endings mediate this response to stress. Capsaicin, found in hot peppers, causes depletion of neuropeptides contained in sensory nerve endings.

We have found that inhibition of the stress response is achieved by pretreating laboratory animals with a blocker of the physiological action(s) of CRH, for example, by an antiserum to this neuropeptide hormone. Although applicant need not be bound by any particular theory of mechanism of action, it is likely that the antibody, by binding to CRH blocks the binding of CRH to its physiological receptor(s).

Other CRH blockers are expected to have the same beneficial effects as the anti-CRH antibody. Examples include an anti-CRH receptor antibody that blocks the binding of CRH to its physiological receptor(s), a competitive or non-competitive CRH antagonist (peptide and neuropeptide) such as the CRH analog Neurocrine Biochemicals, Inc.'s D-Phe12, Nle Ala32 21,38 hCRH (12-41)NH2 (cat. no. 1P-36-41, mw 3474.1) and Pfizer CP-154,526-1 that will compete with CRH for binding to CRH receptor(s), and inhibitors of CRH secretion such as agents that block interleukin-6 and histamine-3 receptors, are also expected to relieve stress-induced migraine headaches.

Although all of the aforementioned CRH blocking agents are expected to be therapeutic against stress-induced migraine headaches, they will be operating by different mechanisms. Therefore, the dosage required of each of these agents to achieve a therapeutically effective concentration in brain must be determined on a case-by-case basis. Such a determination will not require undue experimentation for one skilled in the art.

In the present animal experiments, mast cells in the dura were found to be localized close to nerve processes containing the neuropeptide substance P, but no CRH-positive fibers were identified even though these were found close to mast cells elsewhere in the brain, i.e., in the median eminence. It is suggested that the effect of CRH on the activation of intracranial mast cells is an indirect one, with the primary action of CRH being on the release of sensory neuropeptides such as substance P that then activate brain mast cells.

Several of the techniques used in making the present invention and in determining anti-CRH drug dosages are described below generically:

1. Immobilization restrain stress

Male Sprague/Dawley rats, each weighing approximately 150 g (Taconic, Germantown, N.Y.), are kept in their cage in the laboratory (control) or are restrained for 30 min in a plexiglass immobilizer (Harvard Apparatus, Cambridge) located on a bench top at room temperature (stressed). Each animal is equilibrated to the laboratory environment for 60 min prior to handling. Each rat is then taken through the entire procedure separately and the next rat is not brought in until 60 min after completion of the dissection of the previous one. Consequently, no rat should be present or in close proximity while another is stressed or dissected. At the end of this 60 minute equilibration period, each animal is anesthetized with a single intraperitoneal injection containing 0.5 ml ketamine (20 mg/ml) and 0.5 ml xylazine HCl (20 mg/ml), following which cerebrospinal fluid (CSF) is removed by entering the cisternum magnum with a tuberculin syringe. The brain is then rapidly removed and the dura attached to the skull is fixed by immersion of the skull in 4% paraformaldehyde for 2 hr at room temperature. The dura is then removed carefully en bloc, and fixed in 4% paraformaldehyde overnight at 4° C. It is then frozen using Tissue Freezing Medium (Triangle Biomedical Sciences, Durham, N.C.) and thin sections ($7\mu$) are cut using a cryostat (Jung CM 3000, Leica, Luc. Deerfield, Ill.). The sections are stained with acidified (pH<2.5) toluidine blue (Sigma, St. Louis). Mast cells are counted (by at least two different researchers blinded to the experimental conditions) at 400× magnification, for example, by using a Diaphot inverted Nikon microscope (Don Santo, Natick, Mass.).

2. Immunohistochemistry

All specimens are treated with 0.3% $H_2O_2$ in methanol for 30 min to block endogenous peroxidase. After briefly rinsing in phosphate-buffered saline (PBS), sections are incubated in 5% normal goat serum in PBS for 30 min, and then exposed to rabbit anti-substance P (SP) polyclonal serum (Shimonaka et al., *J. Neurochem.*, 59:81 (1992)) at 1:4000 or to anti-CRH polyclonal serum at 1:100 in PBS containing 5% normal goat serum for 48 hr at 4° C. Visualization of the location for immobilized antigen may be made using the avidin-biotin-peroxidase system (Vector Laboratories, Burlingame, Calif.) and 3',3'-diaminobenzidine as the peroxidase substrate. Negative controls are performed by using anti-SP and anti-CRH serum preabsorbed respectively with 1 $\mu$M SP or CRH as primary antibody (Pang et al., *Br. J. Urol.* 75:744 (1995)).

3. Electron microscopy

Tissue is fixed in modified Karnovsky's medium containing 0.5% tannic acid and processed as previously described (Demitriadou et al., *Neuroscience*, 44:97 (1991)).

4. Capsaicin treatment

Rats are treated within the first 3 days after birth with capsaicin as previously described (Demitriadou et al. above), and are used seven weeks later.

5. Treatment with CRH blockers

Rats are injected parenterally with a CRH blocking agent. For example, with a single 1 ml dose (1 mg protein/ml) of anti-CRH polyclonal serum intraperitoneally one hour prior to being stressed. Companion animals are sham-injected with an equal amount of 0.9% NaCl and are then handled similarly.

The present data clearly demonstrate that stress induces intracranial mast cell activation that appears to result mostly in intragranular changes accompanied by secretion of at least RMCP-I, rather than the massive degranulation by compound exocytosis seen in anaphylactic reactions. Such intragranular changes, often seen in mast cells found in close juxtaposition to neuronal processes, have previously been noted both in the gastrointestinal tract of patients with inflammatory bowel disease (Dvorak et al., *Int. Arch. Allerg. Immunol.*, 98:158 (1992)) and in the urinary bladder of patients with interstitial cystitis (Letourneau et al., *Br. J. Urol.*, in press, 1995). Similar intragranular activation had previously been reported in mast cells undergoing differential release of mediators (Kops et al., *Cell*, 262:415 (1990)) without exocytosis. This type of activation may represent either a unique process and/or an effect due to small concentrations of neuropeptides released at a distance close to that of a typical synapse. In fact, it was recently shown that application of picomolar concentrations of Substance P to mast cells resulted in electrical responses that induced degranulation upon re-exposure (Janiszewski et al., *Am. J. Physiol.*, 267:C138 (1994)).

In the present study, the antiserum to CRH was able to reach the dura because, even though it is intracranial, it is located outside the blood-brain barrier. As no CRH positive nerve processes were present in the dura, it must be concluded that CRH released during stress induces subsequent release of neuropeptides, such as Substance P and calcitonin gene-related peptide (CGRP) stored in sensory nerve endings, which then activate dura mast cells. These neuropeptides have previously been shown to stimulate intracranial mast cell secretion directly (Demitriadou et al., *Pain*, Suppl. 5: Abstr. 14, 1990), and to be partially responsible for neurogenic inflammation in response to antidromic trigeminal ganglion stimulation. In fact, dura mast cell activation by trigeminal ganglion stimulation is abolished by neonatal animal treatment with capsaicin which destroys peptidergic nerve endings (Demitriadou et al., 1991 above).

Peripheral mast cells are known to be activated by many neuropeptides, especially Substance P. Substance P has been shown to induce granulocyte infiltration through mast cell degranulation, thus contributing to neurogenic inflammation. It should be noted that the secretory effect of Substance P is augmented by estradiol, which may partially explain the higher incidence of migraines in women, especially at the time of ovulation. In fact, interstitial cystitis, which also occurs more often in women and is worse at midcycle, is associated with a higher incidence of migraines and is characterized by an increased number of activated mast cells expressing high affinity estrogen receptors. Parasympathetic nerve stimulation can augment or trigger mast cell secretion, while mast cell-derived histamine can then stimulate peripheral neurons, suggesting that mast cell-neuron interactions may be involved in pathophysiology and pathology. Such results have led to the hypothesis that sensory neuropeptides regulate hypersensitivity reactions. In fact, such neuropeptides were shown to have different effects on lymphocyte function and proliferation suggesting that these are specific effects.

CRH has recently been shown to degranulate skin mast cells (Boucher et al., *FASEB J.* Abstract issue, 1995) indicating that there may also be such an effect in tissues where mast cells have access to products of CRH action. This may be true especially in the hypothalamus where mast cell proximity to CRH-positive nerve processes was observed. The facts that mast cells are activated by somatostatin and mast cells secrete interleukin-6 which has been implicated in the control of CRH (Navarra et al., *Endocrinology* 128:37 (1991); Mastorakos et al., *J. Clin. End. Metab.* 77:1690 (1993)), suggests that a functional, albeit indirect, interaction may exist between CRH and mast cells in the hypothalamus. The possibility, therefore, exists that hypothalamic mast cells may also be affected by stress leading to changes in mood and cognitive function. It is, therefore, of interest that atopic diseases occur more frequently in children born to women with migraines and there is a higher incidence of atopic disorders in affective patients.

The present results may explain the pathophysiology of neuroimmunoendocrine disorders, such as migraines, which are clearly exacerbated by stress. Mast cells have been proposed to play a key role in migraines (Theoharides, *Perspect. Biol. Med.* 26:672 (1983)) through the release of vasoactive, nocioceptive and pro-inflammatory molecules (Scutieri, *Headache*, 86 (1963). For instance, histamine elevations have been documented in the serum of patients during migraine. Nitric oxide (NO) has been proposed as a key molecule in the pathogenesis of migraines, and mast cells have been shown to release NO upon stimulation. Dura mast cell degranulation in response to antidromic trigeminal ganglion stimulation is accompanied by vascular changes which are similar to those seen in migraines. Moreover, the clinical efficacy of 5-hydroxytryptamine receptor agonists used to treat migraines corresponds to their ability to block dura mast cell degranulation and neurogenic inflammation (Buzzi et al., *Brain Res.* 583:137 (1992)). Brain mast cell activation in response to stress may also be involved in other neuroinflammatory disorders. For instance, migraines occur more frequently in multiple sclerosis (MS) patients, and the mast cell specific enzyme tryptase was shown to be elevated in the CSF of MS patients.

Stress-induced brain mast cell degranulation, resulting sequentially and functionally from the release of CRH and certain neuropeptides, may prove to be a useful model to further investigate the pathophysiology of migraines and screen for more effective anti-migraine drugs, such as novel CRH receptor antagonists

EXAMPLES

Example 1

Stress and Mast Cell Activation

Mast cell activation, judged by granule content extrusion and loss of cellular staining was present in 69.9±5.3% (n=501) of mast cells in stressed animals (FIG. 1B), as compared to 38.7±5.0% (n=683) in controls (FIG. 1A and Table 1). The data of Table 1 show that this difference was statistically significant (Mann Whitney U-test, P=0.0018; t-test, P<0.05).

TABLE 1

| Brain Dura Mast Cell Activation During Stress | | | | |
|---|---|---|---|---|
| Variable | n | Activation (% total) | P[a] | P[b] |
| Control | 683 | 38.7 ± 5.0 | | |
| Stressed | 501 | 69.9 ± 5.3 | 0.0018 | <0.05 |
| Anti-CRH | 460 | 33.1 ± 4.0 | 0.0007 | <0.05 |
| Capsaicin | 415 | 25.8 ± 8.5 | 0.0016 | <0.05 |

[a]Mann-Whitney U-test comparing the results with the stressed animal to every other condition.
[b]Unpaired t-test
n = Total no. of mast cells studied in a total of 12 rats for each condition tested

Example 2

Effect of Capsaicin Plus CRH Blocker on Mast Cell Activation

In animals that had been pretreated neonatally with capsaicin to destroy sensory nerve termini, stress-induced dura mast cell activation was reduced (Mann Whitney U-test, P<0.0016; t-test, P<0.05) to 25.8±8.5% (n=415) which was below control levels (Table 1).

Pretreatment of animals intraperitoneally with 1 mg/ml of a polyclonal antiserum to CRH for 60 min prior to stress also reduced dura mast cell activation ((Mann Whitney U-test, P<0.0007; t-test, P<0.05) to 33.1±4.0% (n=460) which was slightly below control (Table 1).

The amount of rat mast cell protease (RMCP)-I recovered in the CSF of stressed animals was 5.3±3.1 (n=22) and was significantly higher (Mann Whitney U-test, P=0.009) than that in control animals: 3.8±1.3 (n=11). RMCP-I was undetectable in animals treated with capsaicin (n=3) or with anti-CRH serum (n=4). RMCP II was undetectable in all groups studied.

Example 3

Immunochemistry

Immunohistochemistry, along with metachromatic staining with toluidine blue, showed localization of mast cells adjacent to substance P-immunoreactive nerve fibers in the dura (FIG. 2A stained brown), but no CRH-immunoreactive nerve processes were present in the dura (FIG. 2). However, numerous CRH-positive nerve processes stained golden brown were present close to mast cells in the median eminence (FIG. 2B).

Example 4

Electron Microscopy

Figure 3:
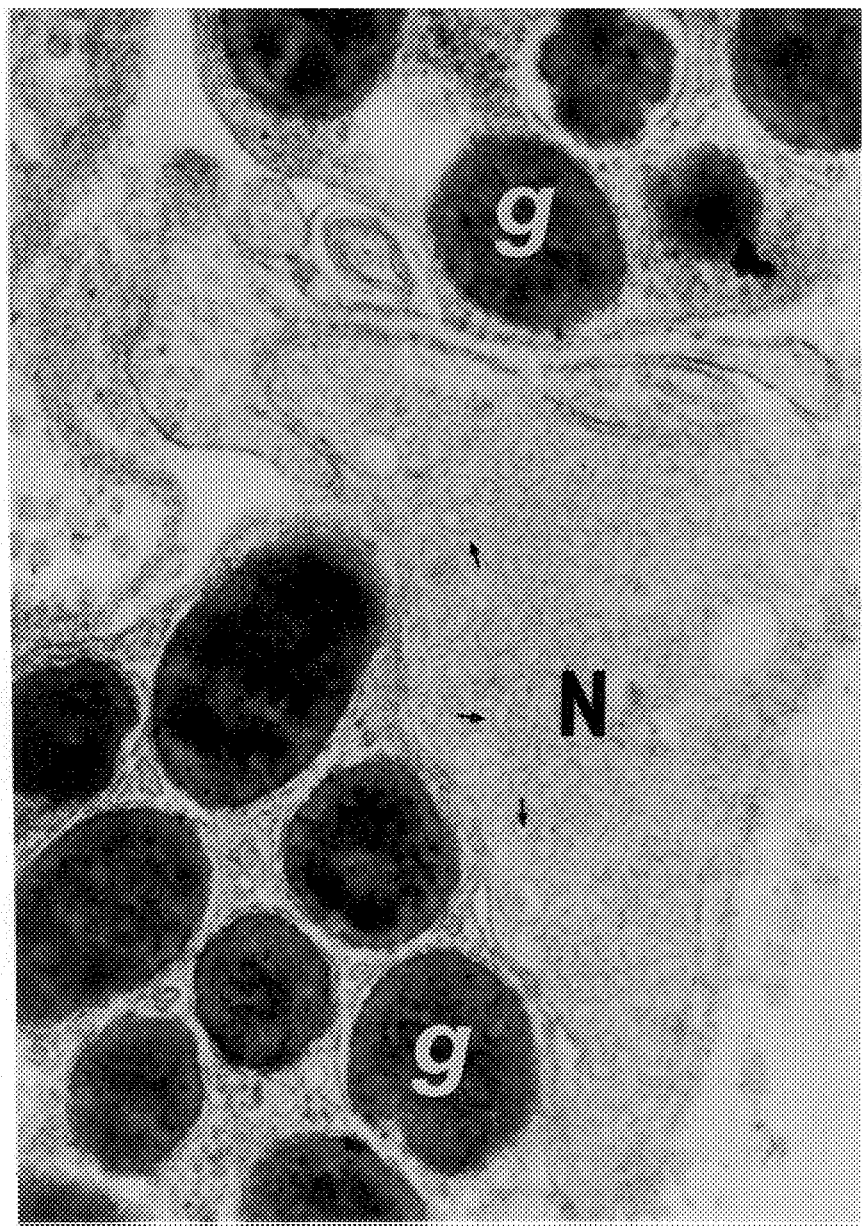
Figure 4A:
Figure 4C:
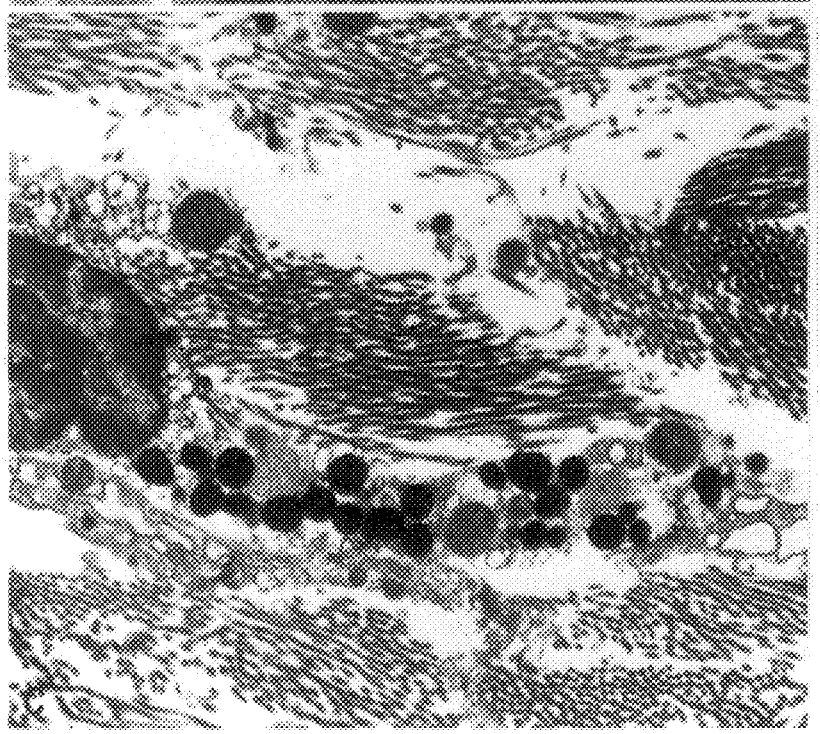
Figure 4B:
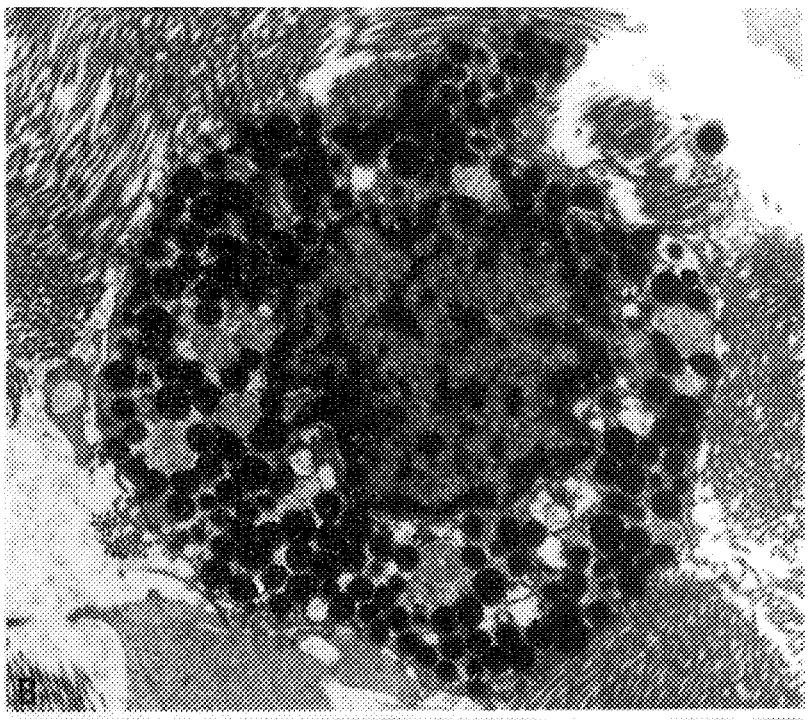
Figure 4D:
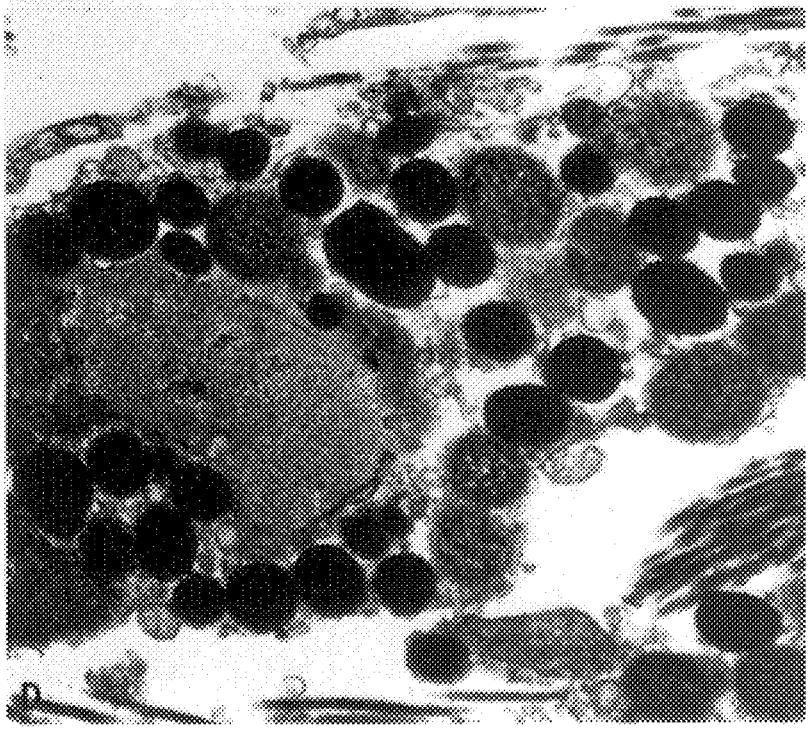

Electron microscopy also captured images of mast cells with signs of subtle intragranular changes surrounding terminal nerve processes (N) containing synaptic vesicles (small solid arrows) (FIG. 3). The ultrastructural appearance of dura mast cells from stressed animals was characterized by extensive alterations of secretory granule (g) electron dense content consistent with secretion. These included partially filled or empty granules, as well as others the content of which had entirely different texture with distinct crystalline or amorphous, nonhomogeneous patterns (FIG. 4).

What is claimed is:

1. A method for treating migraine headaches in a patient comprising the step of administering to said patient an effective amount of a corticotropin releasing hormone (CRH) blocker, wherein said blocker antagonizes a physiological action of CRH.

2. The method of claim 1, wherein said migraine headache is stress induced.

3. The method of claim 1, wherein said blocker is an antibody directed against corticotropin releasing hormone.

4. The method of claim 1, wherein said blocker is an antibody directed against a corticotropin releasing hormone receptor.

5. The method of claim 1, wherein said blocker is a competitive inhibitor of the binding of corticotropin releasing hormone to a receptor.

6. The method of claim 5, wherein said competitive inhibitor is a peptide analog of corticotropin releasing hormone.

7. The method of claim 1, wherein said blocker is a non-peptide analog of corticotropin releasing hormone and, wherein said analog is a competitive or non-competitive inhibitor of a physiological receptor for CRH.

8. The method of claim 1, wherein said blocker is an agent that inhibits the secretion of corticotropin releasing hormone.

9. The method of claim 8, wherein said secretion is from neuronal sources.

10. The method of claim 7, wherein said analog is CP-154,526-1.

11. The method of claim 8, wherein said secretion is from non-neuronal sources.

12. The method of claim 8, wherein said secretion is from the hypothalamus.

* * * * *